(12) United States Patent
Koehler

(10) Patent No.: US 9,161,733 B2
(45) Date of Patent: Oct. 20, 2015

(54) INTERFACE DEVICE, IMAGING SYSTEM AND METHOD FOR RIM-IMAGING

(75) Inventor: Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 974 days.

(21) Appl. No.: 13/148,323

(22) PCT Filed: Feb. 5, 2010

(86) PCT No.: PCT/IB2010/050527
§ 371 (c)(1),
(2), (4) Date: Aug. 12, 2011

(87) PCT Pub. No.: WO2010/092513
PCT Pub. Date: Aug. 19, 2010

(65) Prior Publication Data
US 2011/0311024 A1 Dec. 22, 2011

(30) Foreign Application Priority Data
Feb. 12, 2009 (EP) .................................... 09152631

(51) Int. Cl.
*A61B 6/04* (2006.01)
*G01T 1/36* (2006.01)
*A61B 6/00* (2006.01)
(Continued)

(52) U.S. Cl.
CPC .................. *A61B 6/484* (2013.01); *A61B 6/502* (2013.01); *A61B 5/0091* (2013.01); *A61B 6/0414* (2013.01); *A61B 8/0825* (2013.01)

(58) Field of Classification Search
CPC ...... A61B 6/503; A61B 6/04012; A61B 6/06; A61B 6/4233; A61B 6/0431; A61B 6/484; A61B 5/0091; A61B 6/0414; A61B 6/502; A61B 8/0825; A61B 8/403; A61B 8/4281; A61B 8/4416; A61B 8/582; A61B 8/587; G01N 23/04; C09D 123/06; C09D 161/24; C07K 14/415; C08L 2666/02; C08L 83/00; C12N 15/8216; A61F 13/00008; A61F 13/00034; A61F 13/00063; A61F 13/00068
USPC ............................................... 378/37, 62, 82
See application file for complete search history.

(56) References Cited

U.S. PATENT DOCUMENTS 6,345,194 B1 2/2002 Nelson et al.
8,886,284 B2 * 11/2014 Pogue et al. .................. 600/411
(Continued)

FOREIGN PATENT DOCUMENTS

JP 3128904 U 2/2007
WO WO9806321 2/1998
(Continued)

OTHER PUBLICATIONS

A. Momose, et al., "X-Ray Talbot Interferometry for Medical Phase Imaging", AIP Conference Proceedings, American Institute of Physicas, New York, US, No. 716, Jan. 13, 2004, pp. 156-159.

*Primary Examiner* — Irakli Kiknadze

(57) ABSTRACT

The invention relates to imaging systems in which during imaging of an object a matching medium is used to match the object to its surroundings. An interface device is used for phase contrast rim-imaging of the object, which comprises a compartment in which a deformable matching material is contained which can be pushed to the side when the object to be imaged is compressed. Thus, a lateral field of view for X-ray phase contrast mammography may be increased.

25 Claims, 4 Drawing Sheets

(51) Int. Cl.
  *A61B 5/00* (2006.01)
  *A61B 8/08* (2006.01)

(56) References Cited

U.S. PATENT DOCUMENTS

| 2002/0188198 | A1 | 12/2002 | Hong | |
| 2005/0075048 | A1* | 4/2005 | Legaspi et al. | 450/41 |
| 2005/0245850 | A1* | 11/2005 | Freyre et al. | 601/6 |
| 2005/0286680 | A1 | 12/2005 | Momose | |
| 2006/0039532 | A1* | 2/2006 | Wu et al. | 378/62 |
| 2006/0262898 | A1* | 11/2006 | Partain et al. | 378/37 |
| 2006/0276104 | A1* | 12/2006 | Davis | 450/81 |
| 2009/0135997 | A1* | 5/2009 | Defreitas et al. | 378/37 |
| 2009/0238332 | A1* | 9/2009 | Farrell-Trent | 378/37 |

FOREIGN PATENT DOCUMENTS

| WO | 2004058070 A1 | 7/2004 |
| WO | WO2008053405 | 5/2008 |

\* cited by examiner

INTERFACE DEVICE, IMAGING SYSTEM AND METHOD FOR RIM-IMAGING

FIELD OF THE INVENTION

The invention relates to an interface device for phase contrast rim-imaging of an object of interest, a mammographic imaging system and a method of phase contrast rim-imaging of an object of interest.

BACKGROUND OF THE INVENTION

X-ray phase contrast mammography has the potential to improve the diagnostic value of X-ray mammograms considerably. One special problem with phase-contrast imaging is the so-called phase wrapping problem. For instance, in the measurement setup with a Talbot interferometer with a pitch of $p_1$ for the phase grating, phase information can be retrieved unambiguously only if the gradient of the phase front is less than $2\pi/p_1$. This is typically achievable for a few cm of soft-tissue of constant thickness. However, this is typically not the case at the rim of the object to be imaged (object of interest), where a strong jump of the complex refraction index is present due to the tissue-air interface. This may prevent a proper phase retrieval at the rim of the breast and may hamper thus proper diagnosis at the lateral rim of the breast. Consequently, tomography or tomosynthesis may become difficult, if not impossible.

SUMMARY OF THE INVENTION

It may be desirable to provide for an improved phase contrast rim-imaging of an object of interest.

The invention relates to an interface device for phase contrast rim-imaging of an object of interest, a mammographic imaging system, and a method of phase contrast rim-imaging of an object of interest according to the features of the independent claims. Further features of the invention are stated in the dependent claims.

It should be noted that the features which are in the following described for example with respect to the interface device may also be implemented in the imaging system or, as method steps, in the method according to the invention.

According to an exemplary embodiment of the invention an interface device for phase contrast rim-imaging of an object of interest is provided, the interface device comprising a compartment which comprises a deformable material. The deformable material has a first complex refractive index which corresponds to a second complex refractive index of the object of interest. The compartment and the deformable material are adapted such that the deformable material is pushed away from a region in which a pressure is applied on the compartment when an image data acquisition is performed.

In other words, the interface device is not solid but can change its shape on the basis of an applied pressure. Thus, an improved image quality may be provided, in particular in an outer region of the object of interest, in which no pressure is applied.

According to another exemplary embodiment of the invention, the interface device is adapted rim-imaging in X-ray phase contrast mammography, wherein the object of interest is a human breast.

It should be noted, that the interface device may also be used in optical mammography, where the beam of energy used for probing the object is an optical radiation beam with a wavelength within the range of for example 400 to 1400 nm.

According to another exemplary embodiment of the invention, the interface device is adapted in form of a bra.

According to another exemplary embodiment of the invention, the deformable material is one of a fluid and a gel.

According to another exemplary embodiment of the invention, the first complex refractive index is similar to the second complex refractive index.

According to another exemplary embodiment of the invention, the compartment is formed by two layers of a sheet material designed for having the shape of a human breast when the bra is in a relaxed state. However, the sheet material may have a shape different from the shape of a human breast when the bra is in a relaxed state, for example a shape which corresponds to the final shape of the interface device during compression and image acquisition.

By having two layers of a sheet material, a flexible compartment is provided in which the fluid or gel-like material can move, without touching the breast (or any other object of interest to be imaged).

In particular, the object to be imaged does not need to provide a sealing between the deformable material and the outside environment.

According to another exemplary embodiment of the invention, the deformable material is pushed towards side regions of the object of interest during image acquisition, such that a rim region of the object of interest can be imaged. Without pushing the deformable material towards the side regions (and therefore towards the rim region), the image quality in the rim region of the object of interest would be much poorer.

According to another exemplary embodiment of the invention, a mammographic imaging system is provided, which comprises an interface device for rim-imaging of a human breast and an imaging apparatus. The interface device comprises a compartment comprising a deformable material, wherein the deformable material has a first complex refractive index which corresponds to a second complex refractive index of a breast and wherein the compartment and the deformable material are adapted such that the deformable material is pushed away from a region in which a pressure is applied to the compartment and an image data acquisition is performed. Furthermore, the imaging apparatus comprises an X-ray source for emitting X-rays towards the object of interest and an X-ray detector for detecting the X-rays after they have passed the object of interest. Furthermore, the imaging system comprises a first and a second compression plate, wherein, during image data acquisition, the first and the second compression plates are adapted for applying the pressure to the region of the bra and thus to the breast, thereby pushing the deformable material sideways towards the rim region.

According to another exemplary embodiment of the invention, the detector comprises a Talbot interferometer for determining a phase information of the X-rays after they have passed the object of interest.

Thus, phase data is used for image generation. The X-ray source may be adapted for generating coherent or almost coherent radiation.

According to another exemplary embodiment of the invention, the imaging system is also adapted for determining an absorption of the X-rays due to the object of interest. In other words, the imaging system may not only be adapted for analyzing the phase front of the transmitted wave which predominantly influenced by the real part of the complex refractive index of the object but also the amplitude of the transmitted wave which predominantly influenced by the imaginary part of a the complex refractive index of the object of interest.

Both the phase information and the absorption information may be used for determining the final image.

According to another exemplary embodiment of the invention, the imaging system is adapted for reconstructing an image of the object of interest based on both the determined phase information and the determined absorption information.

This may provide for an improved final image.

According to another exemplary embodiment of the invention, a method of phase contrast rim imaging of an object of interest is provided, in which an interface device is arranged at least partially around the object of interest. Furthermore, a pressure is applied on the interface device, thereby pushing away the deformable material from the region in which the pressure is applied. Then, radiation is emitted towards the object of interest and image data of the object of interest is acquired by one or more corresponding detectors.

According to another exemplary embodiment of the invention, the step of pushing away the deformable material results in an increase of a lateral scan range and thus in an increased image of the object of interest.

According to another exemplary embodiment of the invention, the emitted radiation is X-ray radiation.

According to another exemplary embodiment of the invention, the image acquisition is performed in a Talbot interferometer setup and may, beside of interferometric phase measurements, also comprise absorption measurements.

According to a further embodiment of the interface device, the device comprises two receptacles wherein each receptacle is adapted for receiving one object of interest. This embodiment has the advantage that it enables imaging of two objects simultaneously. When imaging female breasts, a device according to this embodiment can be used to image both breasts simultaneously or to image both breasts sequentially while having to fit the device to the patient only once.

It may be seen as a gist according to an exemplary embodiment of the invention, that a dedicated bra is designed. It consists of two layers. Between the two layers, a fluid or gel-like material is put that has a complex refractive index similar to the breast of the female patient. During compression, the gel is pushed towards the sides. Thus, direct contact of the breast with the two plates is achieved as wanted, but on the sides there is now the gel (or fluid) in addition. Thus, the lateral scan range may be increased and the rim of the breast may be imaged.

DETAILED DESCRIPTION OF EMBODIMENTS

Figure 1:
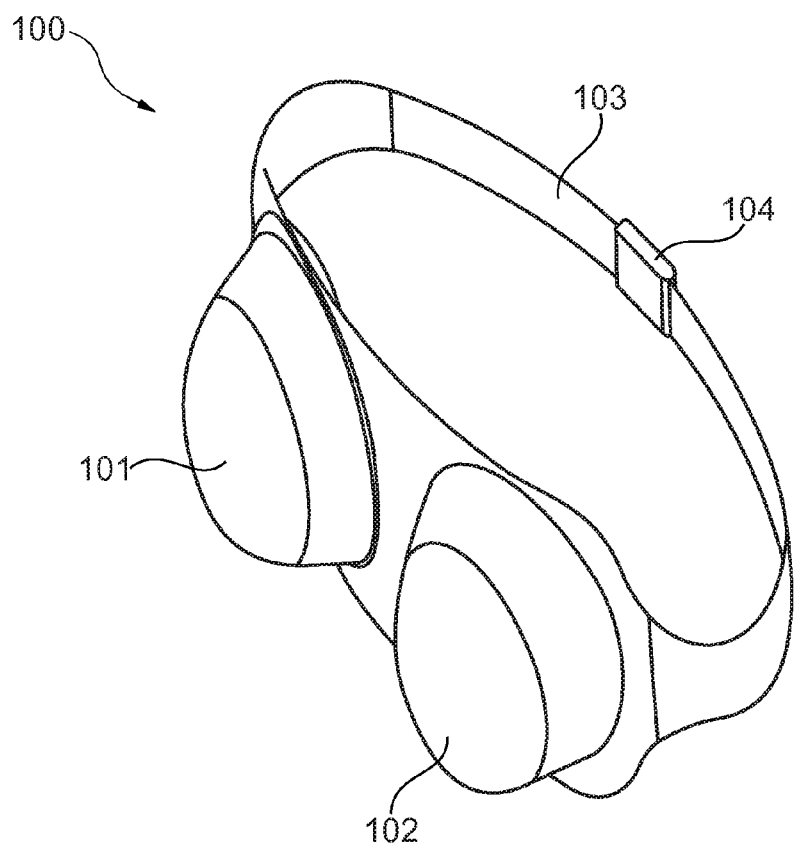
FIG. 1 shows an interface device according to an exemplary embodiment of the invention.

The illustration in the drawings is schematically and not to scale. In different drawings, similar or identical elements are provided with the same reference numerals.

FIG. 1 shows an interface device for phase contrast rim-imaging of an object of interest, in particular for mammographic imaging of two female breasts.

The device 100 comprises two receptacles 101, 102, the first one being for the right breast and the second one being for the left breast of a patient.

Furthermore, the device 100 comprises a strap 103 for forcing the receptacles 101, 102 against the breasts and for securing the device around the chest of the patient. Furthermore, a fastener 104 is provided which is adapted for opening and closing the strap 103.

The strap 103 allows the force with which the device 100 is forced against the breasts to be adjusted allowing for patient comfort. The receptacles 101, 102 may at least partially be flexible to allow them to change the shape in accordance with a boundary bounding a volume for accommodating the receptacles 101, 102. An example of such a boundary are compression surfaces or compression plate between which one or both of the receptacles 101, 102 can be placed when the image is to be taken (i.e. when the acquisition data is to be acquired). Examples for such compression plates 301, 302 are for example depicted in FIGS. 3 and 4.

In each of the receptacles 101, 102 a matching medium (deformable material, for example a gel or a fluid) has been administered. For example, both receptacles may be not only at least partially flexible but also stretchable. An example of an appropriate material for such a receptacle is for example latex, such as the latex used in preservatives (condoms).

Figure 2:
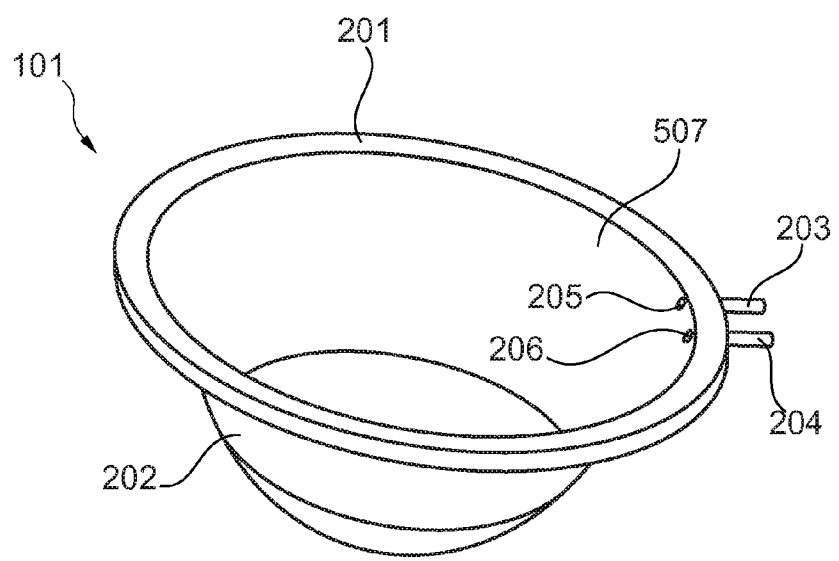
FIG. 2 shows a receptacle of an interface device according to an exemplary embodiment of the invention.

FIG. 2 shows the right receptacle 101 of the bra 100 in more detail. The cup-like device 101 comprises a wall 202 that defines a volume, the "inside" of the cup. The volume defined by the wall 202 has an open side allowing an object to be imaged to be accommodated in the volume. The opening is defined by the rim 201 comprised in the device 101. According to an exemplary embodiment of the invention, the rim 201 comprises an adhesive for fixating the device 101 to the chest of the patient. In this case, using the adhesive comprised in the rim 201, the device 101 is forced against the patient's chest.

The chest, together with the breast accommodated in the device 101 then forms a covering surface that closes the opening defined by the rim 201. In general, an object to be imaged such as a female breast will not completely fill the volume 507 defined by the wall 202. Once the device 101 has been forced against the covering surface (i.e. the chest), the unoccupied volume inside the device 101 is filled with a matching medium, i.e. the deformable material which may for example be a matching fluid or matching gel. For filling the deformable material inside the unoccupied volume a tubular inlet 203 is provided which can be connected to a source for delivering the gel or fluid. The device 101 further comprises an outlet 204 for letting gas, for instance air, escape from the unoccupied volume in order to let the matching medium in.

The source 203 may also be used as a drain to let the matching medium escape from the device 101, for instance after an imaging session when the matching medium is no longer needed. According to an exemplary embodiment of the invention, the matching medium is not filled inside an empty space between the object of interest and the wall 202, but inside a compartment formed by an inner wall (see for example reference numeral 506 in FIG. 5) and the outer wall 202.

No adhesive 201 is necessary in this case.

Figure 3:
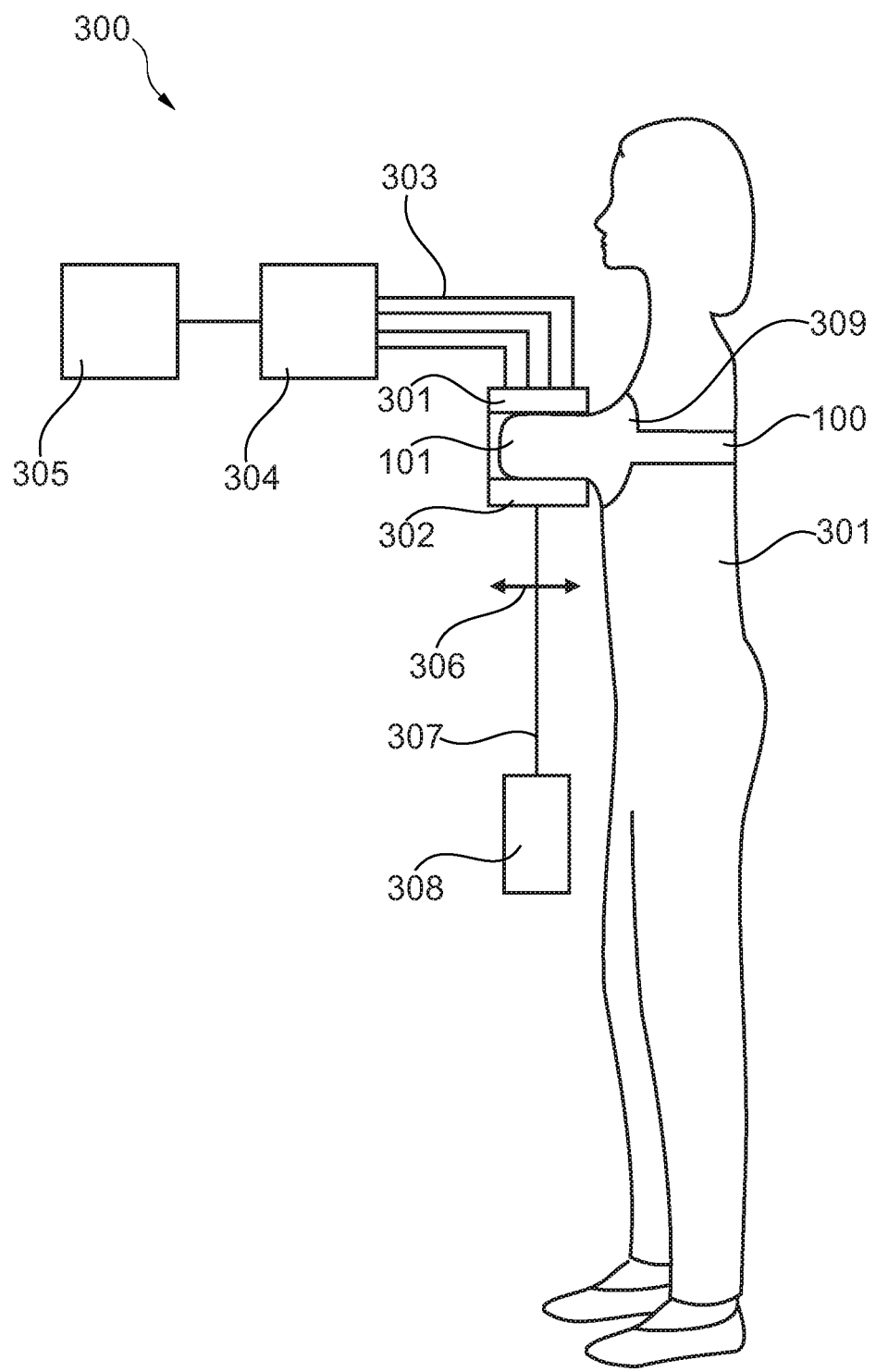
FIG. 3 shows an imaging system according to an exemplary embodiment of the present invention.

FIG. 3 shows an imaging system 300 according to an exemplary embodiment of the invention. A female patient 301 wears an interface device 100 according to the invention over her breasts 309. The imaging system 300 comprises two compression surfaces or compression plates 301, 302 for applying pressure to the patient's breast while the breast is accommodated in the device 101.

The device 300 depicted in FIG. 3 may be used for optical imaging. Coupled to the compression surface 302 is an energy source 308 for generating energy to be used in imaging the patient's breast. The energy generated by the energy source 308 may be, for instance, optical energy or X-rays or ultrasound energy. One technique to image an object of interest, for instance a female breast, is diffuse optical tomography. Another technique is phase contrast x-ray imaging.

In case of optical tomography, the energy source 308 is coupled to the compression surface 302 using an energy guide 307. The energy generated by the energy source 308 can be coupled into the compression surface 302 and, hence, into a patient's breast at various positions as indicated by the double-headed arrow 306. The device 101 is arranged such that energy from the energy source 308 can pass through the receptacle and from there into the object of interest. Similarly, energy can exit the receptacle prior to being detected. Energy emanating from the device 101 passes through the compression plate 301 after which it is detected using detection unit 304. The detection unit 304 is coupled to the compression surface 301 using energy guides 303. Based on the detected energy an image of an interior of the breast is reconstructed using image reconstruction unit 305.

Additional to the absorption information detected by the imaging system 300, also phase information may be measured, therefore, an interferometer is used, which is also implemented in the detection unit 205.

Both the phase information and the absorption information may be used for reconstructing the final image. However, it is also possible to reconstruct the final image from the phase information or the absorption information alone.

Still further, different images may be reconstructed, one on the basis of the phase information, another on the basis of the absorption information and a third image on the basis of both the absorption and phase information.

Figure 4:
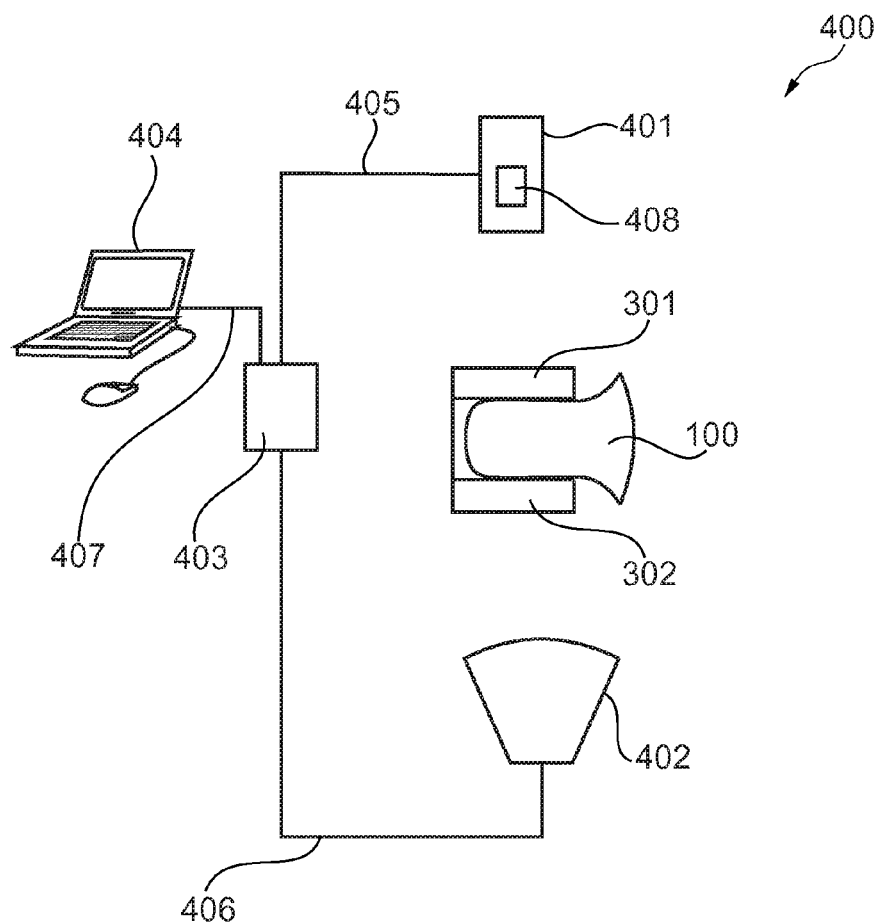
FIG. 4 shows an imaging system according to another exemplary embodiment of the invention.

FIG. 4 shows an imaging system according to another exemplary embodiment of the invention, which comprises an X-ray source 401 emitting an X-ray beam towards the object of interest which is located inside the interface device 100 between the pressure plates 301, 302.

On the other side of the two pressure plates a radiation detector (X-ray detector) 402 is located for detecting the X-ray beams which have passed the object of interest. The detector comprises a Talbot interferometer (408).

Both the source 401 and the detector 402 are connected to a calculation and control unit 403 via data transmission lines 405, 406, respectively. Furthermore, via data line 407, an input and output device 404 is provided, which can be used for inputting control information for controlling the imaging system 400 and which can also be used for outputting visual information relating to the final image.

Figure 5:
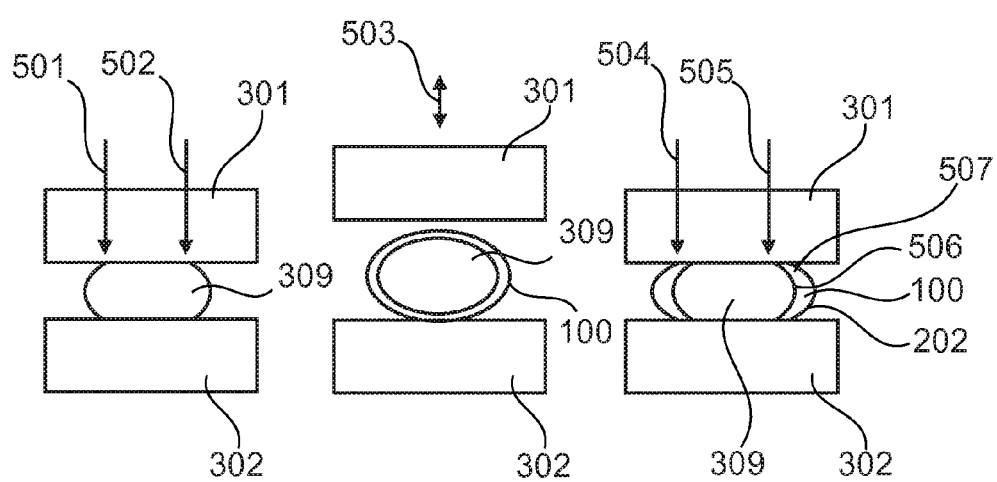
FIG. 5 shows two plates of an imaging device used for compressing the object of interest according to an exemplary embodiment of the present invention.

FIG. 5 shows, on the left side, a compression geometry in which two compression plates or pressure plates 301, 302 are moved towards each other in order to compress a female breast 309. The left and right arrows 501, 502 indicate the borders of the lateral field of view where phase-retrieval is possible. This lateral field is limited to the range where the compressed breast 309 has contact to the two plates 301, 302.

The image in the middle shows a female breast 309 (or any other object of interest to be imaged) at least partially surrounded by an interface device according to the present invention. The interface device 100 comprises a compartment 507 defined by an inner sheet material 506 and an outer sheet material 202 (see right image). The compartment is filled with a deformable material (for example a gel or fluid) which has a complex refractive index similar to the complex refractive index of the object of interest.

The upper pressure plate 301 can be moved upwards and downwards along double arrow 503.

As can be seen in the right image of FIG. 5, the gel or fluid extends the lateral field of view after compression of the interface device, as indicated by left and right arrows 504, 505.

Thus, the lateral field of view for X-ray phase contrast mammography in compression geometry may be increased.

Figure 6:
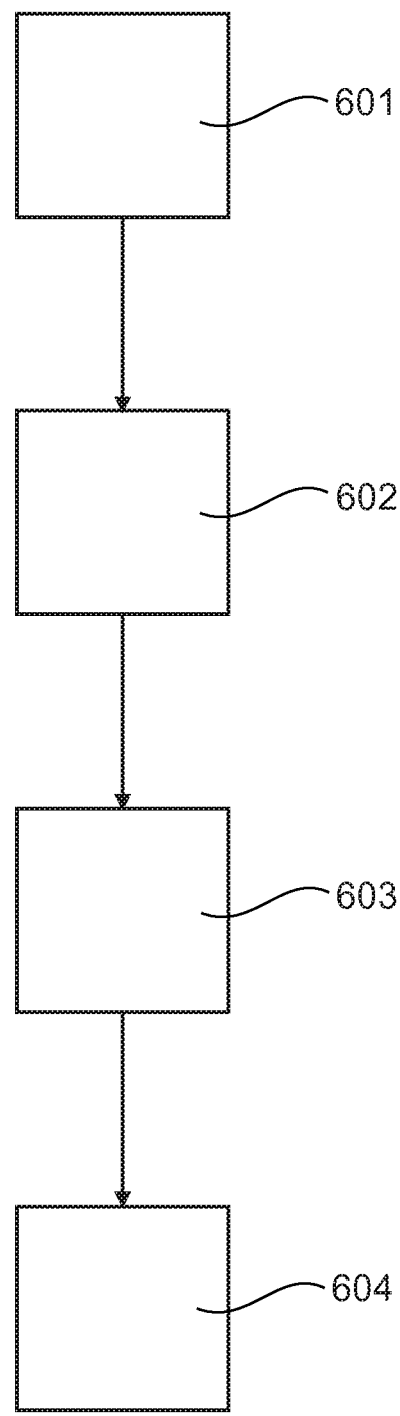
FIG. 6 shows a flow-chart of a method according to an exemplary embodiment of the present invention.

FIG. 6 shows a flow-chart of a method according to an exemplary embodiment of the invention. In step 601 the interface device is arranged at least partially around the object of interest to be imaged. In step 602 a pressure is applied on the interface device and thus on the object of interest, thereby pushing away deformable material from the region in which the pressure is applied towards the rim. In step 603 electromagnetic radiation is emitted from a source towards the object of interest. The radiation source may be a coherent radiation source such that sufficiently accurate phase data can be acquired and analyzed.

Then, in step 604, image data of the object of interest is acquired by using a Talbot interferometer setup.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. An interface device for phase contrast imaging of an object of interest, the interface device comprising: a compartment comprising a deformable material; wherein the deformable material has a first complex refractive index which corresponds to a second complex refractive index of the object of interest; wherein the compartment and the deformable material are adapted such that the deformable material is pushed away from a region in which a pressure is applied on the compartment when an image data acquisition is performed, wherein the interface device is adapted in form of a bra, wherein the compartment is formed by two layers of a sheet material designed for having the shape of a human breast when the bra is in a relaxed state.

2. The interface device of claim 1, wherein, during image data acquisition, the deformable material is pushed towards side regions of the object of interest, such that a rim region of the object of interest is imageable effectively.

3. The device of claim 1, further comprising a PCI processor configured for performing said acquisition, and a pair of compression plates for the applying of said pressure.

4. The device of claim 3, further comprising a calculation and control unit that includes said processor.

5. The device of claim 3, further comprising an X-ray source and an X-ray detector that are communicatively connected to said processor for said performing.

6. A mammographic imaging system, comprising: an interface device for phase contrast imaging of a human breast; a deformable material, and an imaging apparatus; wherein the interface device is adapted as a bra; wherein the deformable material has a first complex refractive index which corresponds to a second complex refractive index of the breast; wherein the interface device and said deformable material are adapted such that the deformable material is pushed away from a region of said bra in which a pressure is applied on the bra when an image data acquisition is performed; and wherein the imaging apparatus comprises: a radiation source for emitting a beam of radiation towards an object of interest; a radiation detector for detecting a phase of the radiation after it has passed the object of interest; a first compression plate and a second compression plate; wherein, during image data acquisition, the first and the second compression plates are adapted for applying said pressure.

7. The imaging system of claim 6, wherein the detector comprises a Talbot interferometer for determining a phase information of the radiation after is has passed the object of interest.

8. The imaging system of claim 7, also adapted for determining an absorption of the radiation due to the object of interest.

9. The imaging system of claim 8, adapted for reconstruction of an image of the object of interest based on both the determined phase information and the determined absorption.

10. The system of claim 6, the pushing away serving to push substantially all of said deformable material laterally, with respect to said breast, away from said region.

11. The system of claim 6, the pushing away resulting in an increase of a lateral scan range and thus in an increased image of said breast.

12. The system of claim 6, wherein the emitted radiation is x-ray radiation, said detecting using x-ray phase contrast mammography.

13. The system of claim 6, said object of interest comprising said breast.

14. An interface device for phase contrast imaging (PCI) of a body part of a patient being examined, the interface device comprising:
a compartment comprising a deformable material having a first complex refractive index which corresponds to a second complex refractive index of said body part; and
wherein said device is configured for, when a PCI image data acquisition is to be performed, compressing, while said body part, of said patient being examined, inserted into said compartment is inside the compartment, said compartment in a particular direction to thereby push said deformable material away in, as a result of the deformability, a lateral direction that is both perpendicular to said particular direction and alongside said patient to thereby, for the compressed body part, extend laterally an effective PCI field of view for rim imaging of said body part.

15. The interface device of claim 14, adapted for rim-imaging in x-ray phase contrast mammography; wherein said body part is a human breast.

16. The interface device of claim 14, wherein the interface device is adapted in form of a bra.

17. The interface device of claim 1, wherein the deformable material comprises a gel.

18. The interface device of claim 14, wherein the first complex refractive index is similar to the second complex refractive index.

19. The device of claim 14, further comprising a pair of compression plates for said compressing.

20. The device of claim 14, further comprising a calculation and control unit, said unit including a PCI processor via which said device acquires said data.

21. The device of claim 14, further comprising an X-ray source and an X-ray detector that are communicatively connected to said processor for the acquiring of said data.

22. The device of claim 14, said deformable material comprising a gel.

23. The device of claim 22, said body part being a breast, said device being configured for mammography using the acquired data.

24. The device of claim 14, said body part being a breast, said device being configured for mammography using the acquired data.

25. The device of claim 14, said compartment being formed by two layers of a sheet material.

* * * * *